| United States Patent [19] | [11] Patent Number: 4,539,405 |
| Willer | [45] Date of Patent: Sep. 3, 1985 |

[54] SYNTHESIS OF 1,4-DINITROFURAZANO(3,4-B)PIPERAZINE

[75] Inventor: Rodney L. Willer, Ridgecrest, Calif.

[73] Assignee: The United States of America as represented by the Secretary of the Navy, Washington, D.C.

[21] Appl. No.: 600,708

[22] Filed: Apr. 16, 1984

[51] Int. Cl.³ .................. C07D 413/02; C07D 498/04
[52] U.S. Cl. .................................. 544/367; 544/382; 564/259; 564/268
[58] Field of Search ............................... 544/367, 358

*Primary Examiner*—Donald G. Daus
*Assistant Examiner*—S. A. Gibson
*Attorney, Agent, or Firm*—Robert F. Beers; W. Thom Skeer

[57] ABSTRACT

The novel explosive compound, 1,4-dinitrofurazano[3,4-b]piperazine, is prepared by the reaction of 2,3-dioximinopiperazine with a base, followed by the nitration of the intermediate furazano[3,4-b]piperazine. The nitrated compound has a density, detonation pressure, detonation velocity and Isp similar to RDX while being highly insensitive.

3 Claims, No Drawings

SYNTHESIS OF 1,4-DINITROFURAZANO(3,4-B)PIPERAZINE

BACKGROUND OF THE INVENTION

B 1. Field of the Invention

This invention relates to a new highly energetic compound.

2. Description of the Prior Art

Hexanitrobenzene is one well known energetic compound. The recently developed compound, 1,4,5,8-tetranitro-1,4,5,8-tetraazadifurazano[3,4-c][3,4-h]decalin, has been found to be more energetic than hexanitrobenzene but lacks thermal stability. Future military ordnance requirements call new energetic materials with higher energy content, increased thermal stability and improved resistance to accidental initiation.

Recent work by the inventor has resulted in the synthesis of a novel insensitive energetic material.

SUMMARY OF THE INVENTION

Accordingly, the present invention provides the insensitive energetic compound, 1,4-dinitrofurazano[3,4-b]piperazine. The method of preparing the compound of this invention comprises converting the dioxime of 2,3-diketopiperazine to furazano[3,4-b]piperazine by the treatment with base. The furazano[3,4-b]piperazine is then nitrated with a mixture of trifluoroacetic anhydride and 100% nitric acid to yield the 1,4-dinitrofurazano[3,4-b]piperazine.

OBJECTS OF THE INVENTION

It is an object of this invention to provide a novel energetic compound.

Another object of the invention is to provide an insensitive energetic compound with thermal stability.

Still another object of this invention is to provide a method of making the compound.

These and other objects, advantages and novel features of the present invention will become apparent from the following detailed description.

DETAILED DESCRIPTION OF THE PREFERRED EMBODIMENT

Recent efforts have resulted in the synthesis of the compound, 1,4-dinitrofurazano[3,4-b]piperazine, shown below.

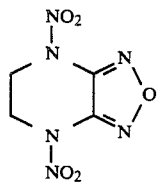

The properties of 1,4-dinitrofurazano[3,4-b]piperazine are similar to the measured properties of RDX: density, 1.806 g/cc; detonation velocity, 8.7 mm/μs; detonation pressure, 338 Kbar. This combination of properties provides an insensitive explosive with excellent explosive properties. Further, theoretical performance calculations of the compound as a monopropellant have yielded a specific performance or Isp of 257.2 N.s/kg. This value compares to an Isp of about 263-264 N.s/kg for HMX and RDX. The insensitivity of the 1,4-dinitrofurazano[3,4-b]piperazine in combination with the high Isp gives the compound excellent propellant properties.

The following examples illustrate the synthetic route.

EXAMPLE 1

A solution of 139 g (2 moles) of hydroxylamine hydrochloride in 100 ml of water was prepared in a one-liter Erlenmeyer flask. To this solution was added 145 g (1 mole) of 40% aqueous glyoxal. The solution was then stirred and 106 g (1 mole) of solid sodium carbonate was added in small portions over a 2 hour period. The resulting mixture was stirred for 1 hour at room temperature. The reaction mixture was then heated to reflux to dissolve the crude product. The solution was allowed to cool slowly to 0° C. The product, glyoxime, was then collected by vacuum filtration. The crude product weighed 70-75 g (80-88%) and melted at 172°-174° C.

EXAMPLE 2

Glyoxime (17.6 g, 0.2 mole) and ethanol (200 ml, 95%) were placed in a one-liter, three-neck flask equipped with a mechanical stirrer, gas inlet tube, and a bubbler. While this mixture was maintained at −20° C. and stirred, chlorine gas ($\approx$35 g) was bubbled into the mixture over a 30 minute period. The mixture was stirred for 20 additional minutes, then the solvent was removed at reduced pressure to give the crude product. The crude product, dichloroglyoxime, was slurried with 100 ml chloroform and then it was collected by vacuum filtration. The product, dichloroglyoxime, weighed 24.2-30.2 g after drying (77-97%).

EXAMPLE 3

Dichloroglyoxime (15.7 g, 0.10 mole) and methanol (400 ml) were placed in a one-liter, round-bottom flask. This solution was cooled to 5° C. by means of a salt-ice bath. While the solution was vigorously stirred, a solution of 12.0 g (0.20 mole) of ethylene diamine in 30 ml of methanol was added in one portion. The mixture was stirred for 10 minutes; then the solvent was removed at reduced pressure. The remaining solid was slurried with 20 ml of water and the crude 2,3-dioximinopiperazine was collected and washed with methanol. The crude product weighed 10.2 g (70%). It can be recrystallized from water (70% recovery) to give the pure compound, 2,3-dioximinopiperazine, with a melting point of 195°-196° C. (dec).

EXAMPLE 4

Twenty ml of ethylene glycol and 3.2 g (0.08 moles) of sodium hydroxide were placed in a 100-ml, round-bottom flask. This was stirred at 150° C. until the sodium hydroxide dissolved, then 11.52 g (0.08 mole) of dioximopiperazine was added in small portions over a 2-3 minute period. The reaction was stirred at 150° C. until everything dissolved (10-20 minutes), then the mixture was cooled and diluted with 20 ml of water. The cooled, diluted reaction mixture was stirred for 1 hour at 0° C., then the crude product was collected by vacuum filtration. The crude product was not washed but was transferred to an Erlenmeyer flask and recrystallized from a minimum amount of water to give the pure furazano[3,4-b]piperazine as light yellow needles with a melting point of 153°-155° C. The yield was 4.72-5.22 g (47-52%).

Analysis calculated for $C_4H_6N_4O$: C, 38.09; H, 4.80; N, 44.43. Found: C, 38.09; H, 5.02; N, 44.35.

EXAMPLE 5

Fourteen ml of trifluoroacetic anhydride and a magnetic stirring bar were placed in a 100-ml, round-bottom flask. The anhydride was cooled to −30° C. (dichloroethane dry-ice) and 6 ml of 100% nitric acid was added dropwise over a 2-minute period. The cooling bath was removed and the mixture allowed to warm to 0° C. The mixture was recooled to −30° C. and 2.52 g (0.02 moles) of furazano[3,4-b]piperazine was added in small portions over a 5-minute period. The cooling bath was removed and the mixture allowed to come to room temperature over 30 minutes. The volatiles were then removed at reduced pressure to give the crude product of 3 as 2.87–3.12 g (66–75%). The product, 1,4-dinitrofurazano[3,4-b]piperazine, was recrystallized from acetone-water to yield platelets with a melting point of 122°–124° C. (dec).

Analysis calculated for $C_4H_4H_6O_5$: C, 22.23; H, 1.87; N, 38.39. Found: C, 22.40; H, 2.00; N, 38.80.

The physical and chemical properties of 1,4-dinitrofurazano[3,4-b]piperazine are summarized in Table 1. The impact sensitivity of 162 cm compares to an impact sensitivity of 92 cm for 2,4,6-trinitrotoluene (TNT) on the available Model 12 impact machine (2.5 kg drop weight). The measured values for detonation pressure and detonation velocity were calculated from the measured density and heat of formation using the method of Kamlet and Jacobs, J. of Chem. Physics, v. 48; 23–25 (1968). The predicted values were obtained by the Rothstein method, Prop. and Explo., v. 4, 56 (1979) and v. 6, 91–93 (1981).

TABLE 1

| Properties | Measured | Predicted |
| --- | --- | --- |
| Melting point, °C. | 122–123 (dec) | — |
| Density, g/cc | 1.828 | 1.82 |
| Heat of formation (Kcal/mole) | +69.0 | — |
| Detonation velocity (mm/μsec) | 8.53 | 8.72 |
| Detonation pressure (Kbar) | 325 | 358 |
| Impact sensitivity (2.5 Kg Wt) | 162 cm | — |

Obviously, many modifications and variations of the present invention are possible in light of the above teachings. It is therefore to be understood that, within the scope of the appended claims, the invention may be practiced otherwise than as specifically described.

What is claimed is:

1. 1,4-dinitrofurazano[3,4-b]piperazine
2. The process of preparing 1,4-dinitrofurazano[3,4-b]piperazine comprising the steps of:
   reacting 2,3-dioximinopiperazine with a strong base to form the product furazano[3,4-b]piperazine;
   nitrating said furazano[3,4-b]piperazine to form said 1,4-dinitrofurazano[3,4-b]piperazine.
3. The process according to claim 2 wherein said 2,3-dioximinopiperazine is prepared by the steps of:
   mixing glyoxime and a solvent to obtain a reaction mixture;
   chlorinating said glyoxime to obtain dichloroglyoxime; and
   reacting said dichloroglyoxime with ethylene diamine to obtain said 2,3-dioximinopiperazine.

* * * * *